(12) United States Patent
Russo et al.

(10) Patent No.: US 9,878,181 B2
(45) Date of Patent: Jan. 30, 2018

(54) METHOD AND DEVICE FOR COMPUTING PHYSICAL AND/OR RADIOBIOLOGICAL QUANTITIES INDUCED BY AN ION BEAM IN A VOLUME

(71) Applicants: Ion Beam Applications S.A., Louvain-la-Neuve (BE); Instituto Nazionale di Fisica Nucleare, Frascati (IT); Internet-Simulation Evaluation Envision SRL, Turin (IT)

(72) Inventors: Germano Russo, Alpignano (IT); Andrea Attili, Turin (IT); Flavio Pietro Marchetto, Borgaro Torinese (IT); Damien Bertrand, Dhuy (BE); Faiza Bourhaleb, Turin (IT)

(73) Assignees: Instituto Nazionale Di Fisica Nucleare, Frascati (IT); Ion Beam Applications S.A., Louvain-La-Neuve (BE); Internet-Simulation Evaluation Envision SRL, Turin (IT)

( * ) Notice: Subject to any disclaimer, the term of this patent is extended or adjusted under 35 U.S.C. 154(b) by 290 days.

(21) Appl. No.: 14/834,059

(22) Filed: Aug. 24, 2015

(65) Prior Publication Data
US 2016/0059042 A1 Mar. 3, 2016

Related U.S. Application Data

(60) Provisional application No. 62/045,334, filed on Sep. 3, 2014.

(51) Int. Cl.
*A61N 5/10* (2006.01)

(52) U.S. Cl.
CPC ......... *A61N 5/1075* (2013.01); *A61N 5/1031* (2013.01); *A61N 5/1043* (2013.01);
(Continued)

(58) Field of Classification Search
CPC .. A61N 5/1075; A61N 5/1031; A61N 5/1043; A61N 5/1081; A61N 2005/1076; A61N 2005/1087
(Continued)

(56) References Cited

U.S. PATENT DOCUMENTS

| | | | |
|---|---|---|---|
| 2006/0231773 A1* | 10/2006 | Katagiri | H01J 41/12 |
| | | | 250/492.1 |
| 2007/0075240 A1* | 4/2007 | Hieke | H01J 49/04 |
| | | | 250/282 |
| 2008/0121798 A1* | 5/2008 | Hieke | H01J 49/145 |
| | | | 250/288 |

FOREIGN PATENT DOCUMENTS

WO 2012/032609 3/2012

OTHER PUBLICATIONS

Extended European Search Report, issued by the European Patent Office in connection with European Patent Application No. 14183916.7, dated Feb. 23, 2015, 4 pages.
(Continued)

*Primary Examiner* — Nicole Ippolito
(74) *Attorney, Agent, or Firm* — Hanley, Flight & Zimmerman, LLC (57) ABSTRACT

The method of the invention comprises the steps of: providing a reference ion beamlet; determining in a phantom (60) a distribution of a linearly-superposable quantity representing a linearly-superposable effect induced by said reference ion beamlet; approximating an ion beam (10) as a weighted superposition of ion beamlets (15), said weighted superposition comprising weight coefficients, at least one ion beamlet (15) being obtained by applying a roto-translation operation to said reference ion beamlet; determining a roto-translated distribution of a linearly-superposable quantity by roto-translating said distribution of a linearly-superposable quantity with said roto-translation operation; deter-
(Continued)

mining said physical and/or radiobiological quantities by performing a weighted superposition comprising said weight coefficients, and said roto-translated distribution of a linearly-superposable quantity.

15 Claims, 2 Drawing Sheets

(52) U.S. Cl.
CPC ............... *A61N 2005/1076* (2013.01); *A61N 2005/1087* (2013.01)

(58) Field of Classification Search
USPC ......... 250/396 R, 397, 492.1, 492.2, 492.21, 250/492.22, 492.23, 492.3
See application file for complete search history.

(56) References Cited

OTHER PUBLICATIONS

Clasie et al., "Golden beam data for proton pencil-beam scanning," Physics in Medicine and Biology, Feb. 14, 2012, 13 pages.

Fuchs et al., "A pencil beam algorithm for helium ion beam therapy," Medical Physics, the International Journal of Medical Physics Research and Practice, Oct. 17, 2012, 13 pages.

Gemmel et al., "Calculation and experimental verification of the RBE-weighted dose for scanned ion beams in the presence of target motion", Physics in Medicine and Biology, vol. 56, No. 23, Nov. 2, 2011, 12 pages.

Grevillot et al., "A Monte Carlo pencil beam scanning model for proton treatment plan simulation using GATE/GEANT4," Physics in Medicine and Biology, Jul. 26, 2011, 18 pages.

Kanematsu et al., "Dynamic splitting of Gaussian pencil beams in heterogeneity-correction algorithms for radiotherapy with heavy charged particles," Physics in Medicine and Biology, Mar. 12, 2009, 14 pages.

Krämer et al., "Treatment planning for heavy-ion radiotherapy: calculation and optimization of biologically effective dose," Physics in Medicine and Biology, May 4, 2000, 13 pages.

Ludewigt et al., "Accelerated helium-ion beams for radiotherapy and stereotactic radiosurgery," Medical Physics, vol. 18, No. 1, Jan. 1991, 8 pages.

\* cited by examiner

METHOD AND DEVICE FOR COMPUTING PHYSICAL AND/OR RADIOBIOLOGICAL QUANTITIES INDUCED BY AN ION BEAM IN A VOLUME

RELATED APPLICATION

This application claims the benefit of U.S. Provisional Patent Application No. 62/045,334, filed on Sep. 3, 2014, which is entitled "Method and Device for Computing in a Volume Physical and/or Radiobiological Quantities Induced by an Ion Beam," and which is hereby incorporated by reference in its entirety.

FIELD OF THE INVENTION

According to a first aspect, the invention relates to a method for computing in a volume (a patient for instance) physical and/or radiobiological quantities induced by an ion beam. According to a second aspect, the invention relates to a device for computing in a volume (a patient for instance) physical and/or radiobiological quantities induced by an ion beam.

DESCRIPTION OF PRIOR ART

Particle therapy is used in a number of cancer treatments. Particle therapy generally uses ion beams (or ionizing beams) for killing abnormal masses of tissue such as tumors. Examples of ion beams are: protons beams and beams of heavier ions such as carbon ions. One important aspect of particle therapy is to find a best experimental procedure for inducing in each patient desired effects while minimizing in the same time undesired effects. For instance, when planning a particle therapy treatment, it is often required maximizing the deposited dose in a tumor while minimizing it into healthy tissues. A Treatment Planning System (TPS) is a set of tools allowing the transcription of desired effects in the patient (such as a dose prescription) into a set of control parameters of the beam line that is used for radiation, such as for instance: energy (or energies) of the ion beam, geometry (position, orientation, divergence for instance) of the ion beam, intensity of the ion beam. A key component of a TPS is a Dose Engine Kernel (DEK) that allows computing effects (such as the deposited dose) induced by an ion beam entering a volume when said ion beam has preset control parameters.

Particle therapy using carbon ions has been developed in last decades and is more and more seen as an advantageous alternative to particle therapy using protons (proton therapy), notably due to the higher death rate of tissue when using carbon ions. There is therefore a need to provide a DEK that could be used for determining effects induced by either a proton beam or a beam of ions such as carbon ions. When using carbon ions, radiobiological quantities such as biological dose or Relative Biological Effectiveness (RBE) for instance are particularly important to determine, as it is known by the one skilled in the art. There is therefore also a need to provide a DEK that could compute both physical and radiobiological quantities. There is also a need for a flexible DEK that could easily determine physical and radiobiological quantities for different beamlines (or different treatment centers).

SUMMARY OF THE INVENTION

According to a first aspect, it is an object of the invention to provide a flexible method for computing in a volume physical and/or radiobiological quantities induced by an ion beam. To this end, the inventors propose the following method: method for computing in a volume a physical or a radiobiological quantity representing an effect induced by an ion beam entering said volume, said method comprising the steps of:
a) providing a reference ion beamlet representing an elementary ion beam;
b) determining in a phantom a distribution of a linearly-superposable quantity representing a linearly-superposable effect induced by said reference ion beamlet entering said phantom;
c) approximating said ion beam as a weighted superposition of ion beamlets,
   i) one of said ion beamlets being a roto-translated ion beamlet that is obtained by applying a roto-translation operation to said reference ion beamlet, a roto-translation operation comprising an operation of rotation and/or translation,
   ii) said weighted superposition comprising weight coefficients;
d) applying the roto-translation operation of step c)i) to the distribution of a linearly-superposable quantity of step b) for obtaining a roto-translated distribution of same linearly-superposable quantity representing an effect induced by the roto-translated ion beamlet of step c)i);
e) performing a weighted superposition comprising the roto-translated distribution of previous step (ie the roto-translated distribution of the linearly-superposable quantity), and weight coefficients of step c)ii) (preferably all the weight coefficients of step c)ii)), for obtaining said physical or radiobiological quantity.

The volume is preferably a part of a patient's body. The volume can be a tumor for instance. Nevertheless, the volume can be a larger volume comprising a tumor. Preferably, the ion beam is characterized by a phase space. Preferably, the phase space of the ion beam is then determined from measurements. It follows that calibration of the method of the invention is easily carried out, for instance during commissioning of the beam line Preferably, more than one ion beamlet of step c) is a roto-translated ion beamlet. For instance, a hundred ion beamlets of said weighted superposition are roto-translated ion beamlets. Still more preferably, each ion beamlet of the weighted superposition of step c) is a roto-translated ion beamlet. Preferably, the approximation of the ion beam in step c) is performed in a medium upstream the volume along main trajectory of the ion beam. Still more preferably, said approximation is performed at an entrance of said ion beam in said volume.

The weighted superposition of step e) could be interpreted as a convolution method. The weight coefficients of the method of the invention take into account, reflect, or include physical properties of the ion beam, in particular properties related to its propagation before reaching the volume. By performing various weighted superpositions with said weight coefficients, the method of the invention allows computing various physical and radiobiological quantities. And this can be carried out with only one global mathematical formulation and with same weight coefficients. For computing different physical or radiobiological quantities, one may choose different linearly-superposable quantities of step b). The linearly-superposable quantity (or linear-superposable quantities) of step b) is preferably determined in advance and saved in a library. More than one weighted superposition generally needs to be performed in step e) for determining some physical or radiobiological quantities that are non linear. This is explained in greater details below. In other words, the inventors have determined a global transfer function that applies to various physical and radiobiological quantities. Input quantity (or input quantities) is (are) the linearly-superposable quantity (or linear-superposable quantities) that is (are) preferably determined in advance and stored in a library, and output quantities (physical and/or radiobiological quantities) are obtained by applying this global transfer function to this (these) input quantity (quantities). Preferably, a calibration procedure allows taking into account the specificities of the used beam line, for instance for determining a phase space of the ion beam. More preferably, this calibration procedure allows determining phase space of the ion beam at its entrance in said volume. With the method of the invention, commissioning time is reduced as only one calibration procedure needs to be performed for various physical and radiobiological quantities. Last, the method of the invention allows saving money as user operation time is reduced.

The method of the invention allows computing physical and/or radiobiological quantities. And it can compute such quantities in a flexible manner: there is only one formulation for different beamlines, for different patients, and for such different quantities. Specificities of different beamlines can be taken into account by the weight coefficients.

The linearly-superposable quantities have to be determined just once for different patients and/or for different beamlines (or different treatment centers). This is also possible thanks to the use of said weight coefficients that take into account, reflect and include physical properties of the ion beam, such as its propagation properties. Hence, the method of the invention is simple and allows a fast computation of physical and/or radiobiological quantities for different patients and different beamlines: a major part of computation (determination of the linearly-superposable quantities) can be carried out in advance. For taking into account the specificities of the used beamline, one only needs to know phase space of the ion beam for instance (preferably at the entrance of the volume that is preferably a patient) for determining the weight coefficients, and to perform steps c) to e). Preferably, the linearly-superposable quantities are determined in advance and stored in a universal library. Preferably, a phase space of the ion beam is determined by a calibration procedure that is preferably performed during commissioning, i.e. before actual computation of physical and/or radiobiological quantities in the volume. The method of the invention is therefore more efficient, and more rapid than other methods.

The method of the invention allows computing physical and/or radiobiological quantities in three dimensions contrary to other methods that can only compute some quantities in one or two dimensions. Some methods allow computing physical and/or radiobiological quantities in three dimensions, but with arbitrary assumptions of lateral dependence of some quantities, for instance with arbitrary assumptions of a lateral dependence of radiobiological quantities. That means that such assumptions are neither related to measurements nor to simulations. This is not the case with the method of the invention that is therefore more precise. The method of the invention is also more stable than other methods.

The method of the invention is also more precise than other methods as different aspects for modeling an ion beam can be taken into account. For instance, in a preferred embodiment where the ion beam is characterized by a phase space, said phase space is assumed to comprise a longitudinal part (generally named longitudinal phase space or energy-related phase space), and a transversal part (generally named transversal phase space). These terms are known by the one skilled in the art. Then, energy distribution and/or transversal phase space of the ion beam can be taken into account for determining said physical and/or radiobiological quantities.

The method of the invention can be used when the ion beam is a beam of protons, or a beam of other ions such as carbon ions. The method of the invention is accurate without requiring long and heavy calculations. The method of the invention is not constrained to analytical formulations. With the method of the invention, transverse effects due to scattering of particles are taken into account and modulate properly a radiobiological effect.

In step a), more than one reference ion beamlet could be provided. Then, the different reference ion beamlets preferably have different energy distributions or different energies. More preferably, each reference ion beamlet of step a) has a well-defined different energy. Preferably, more than one distribution of a linearly-superposable quantity is determined in step b). In particular, it is possible to determine different distributions that correspond to different linearly-superposable quantities. This is particularly useful when using the method of the invention for computing a non-linear physical or radiobiological quantity. This is explained in greater details in the description. In step e), it is possible to perform more than one weighted superposition. For some physical or radiobiological quantities (that are non-linear for instance), it is indeed necessary to perform several weighted superpositions, and thereafter to express said physical or radiobiological quantities as a function of such weighted superpositions. This is also explained in greater details in the description. Therefore, the method of the invention also allows computing non-linear effects (or non-linear physical or radiobiological quantities).

In step b) of the method of the invention, interpolation operations can be used for determining a linearly-superposable quantity induced by a reference ion beamlet. Indeed, if one knows for instance a linearly-superposable quantity induced by two reference ion beamlets that are characterized by two different energies, one can obtain the corresponding linearly-superposable quantity induced by a reference ion beamlet whose energy lies in between these two different energies by applying an interpolating operation to these linearly-superposable quantities induced by these two reference ion beamlets. Said linearly-superposable quantities induced by these two reference ion beamlets can be determined in advance, for instance thanks to numerical simulations, and thereafter saved in a database. More elaborate interpolation operations involving for instance more than two linearly-superposable quantities can be used in step b) for determining a distribution of a linearly-superposable quantity induced by a reference ion beamlet entering the phantom.

Preferably, each reference ion beamlet is characterized by a different minor phase space that is characterized by a minor transversal spread, by a minor energy distribution, and by a minor divergence. Preferably, said minor transversal spread of each reference ion beamlet is equal to or smaller than the (main) transversal spread of the phase space of the ion beam. Preferably, said minor energy distribution is equivalently or less-extended in energy than energy distribution of phase space of the ion beam. Preferably, said minor divergence is zero: that means that in this preferred embodiment, each reference ion beamlet has zero-divergence.

Preferably, the ion beam is a pencil beam whose main direction of propagation can be modified by using scanning systems that are known by the one skilled in the art. Such scanning systems allow treating a volume of finite but non-zero spatial extension (such as a whole volume of a tumor) even if a pencil ion beam is used. Preferably, such scanning systems comprise scanning magnets.

Preferably, said phantom is a water phantom.

Examples of roto-translation operations are: a single rotation, a single translation, a combination of a rotation and a translation.

In step b), said linearly-superposable quantity is preferably induced by a reference ion beamlet entering the phantom along a direction substantially perpendicular to a boundary surface of said phantom. More preferably, said linearly-superposable quantity is induced by a reference ion beamlet entering the phantom along a direction perpendicular to a boundary surface of said phantom.

Preferably, said ion beam is characterized by a phase space, and said weight coefficients of step c)ii) are determined from a discretization of said phase space.

Preferably:
said phase space of said ion beam comprises a longitudinal phase space, $f_L$, comprising an energy distribution, $g(E)$; and
said weight coefficients comprise energy weight coefficients, $g_{E,l}$, determined from a discretization of said energy distribution, $g(E)$.

With this preferred embodiment, it is possible to easily take into account an energy distribution of ion beam that has a non-zero extension in energy.

Preferably:
said phase space of said ion beam comprises a longitudinal phase space, $f_L$, comprising a main Water Equivalent Thickness (WET) distribution, $w(z)$, for taking into account presence of a material traversed by said ion beam (10) before reaching said volume; and
said weight coefficients comprise WET weight coefficients, $w_l$, determined from a discretization of said main WET distribution, $w(z)$.

With this preferred embodiment, it is possible to easily take into account presence of material along the path of the ion beam. This may be an unwanted side effect of some components of the beam line, as it is the case for instance for a beam extraction window at the end of an accelerator vacuum pipe, for air surrounding a nozzle or a patient, beam monitors. The presence of such elements can be modeled with water equivalent thicknesses (WETs). On the other hand, some passive material may be placed on purpose on the beam path with the intent of modifying the energy spectrum, for instance range shifters, or collimators. Another example is an energy-selection system of cyclotron-based beam lines, usually implemented with the insertion of some passive element followed by some kind of monochromator. Another example is a ripple filter in carbon ion therapy, whose role is to enlarge the Bragg peak width for rendering possible a homogeneous irradiation with less spots. The energy straggling caused by all these factors is usually within a few MeV. When the interaction with passive elements is the main source of longitudinal peak modulation, the representation through only an energy spectrum is not the most efficient. A description that considers a probability distribution of Water-Equivalent Thicknesses (WETs) or a main WET distribution of ion beam is rather preferred.

Preferably said phase space of said ion beam comprises a transversal phase space, and said weight coefficients comprise transversal weight coefficients determined from a discretization of said transversal phase space and preferably from beam optics calculations. Beam optics calculations consider or take into account a correlation between ions positions and ions directions. This allows increasing the precision of the method of the invention.

Preferably, the method of the invention further comprises a step of scaling for taking into account differences in path lengths when said ion beam enters said phantom or when it enters said volume.

Preferably, the method of the invention further comprises the steps of determining a water equivalent path mapping between path lengths (of an ion beam or of an ion beamlet) in said volume and path lengths (of an ion beam or of an ion beamlet) in said phantom, and applying said water equivalent path mapping to the distribution of a linearly-superposable quantity of step b). According to another preferred embodiment, an equivalent path mapping is applied to the roto-translated distribution of step d). According to another still preferred embodiment, the water equivalent path mapping is applied to the result of step e). With these preferred embodiments, it is possible to take into account different propagation properties of said ion beam in said volume and in said phantom.

Preferably, said distribution of a linearly-superposable quantity is a dose distribution.

Preferably, said distribution of a linearly-superposable quantity is determined in step b) with Monte Carlo simulations. Then, high precision can be achieved. As said linearly-superposable quantity can be calculated in advance, it is also possible to combine both high precision of Monte Carlo simulations and rapidity of computation. Monte Carlo simulations have other advantages such as for instance:
  direct possibility of dealing with different types of ions constituting said ion beam;
  access to detailed information, in particular to detailed physical information;
  updated and benchmarked knowledge about fragmentation cross sections. This is particularly useful when computing radiobiological quantities.

Monte Carlo simulations are an example of a numerical method for determining the linearly-superposable quantities. A numerical method has the advantage of high flexibility. Other numerical method could be used for determining the linearly-superposable quantities.

Preferably, said distribution of a linearly-superposable quantity is a distribution of mean dose per unit fluence. Preferably, said distribution of a linearly-superposable quantity is a mean track fluence per primary. More preferably, said distribution of a linearly-superposable quantity is a mean energy transfer density per primary. Still more preferably, said distribution of a linearly-superposable quantity is a mean dose-weighted energy transfer density per primary. Then, one can determine for instance three-dimensional Linear Energy Transfer (LET) quantities induced by the ion beam, by expressing them as functions of such linearly-superposable quantities.

Preferably, said distribution of a linearly-superposable quantity is an average number of lethal events per primary depending on α, where α is a parameter entering a Linear-Quadratic law for taking into account radiobiological effectiveness of an ion beam. Preferably, said distribution of a linearly-superposable quantity is a square root of average number of lethal event per primary depending on β, where β is a parameter entering a Linear-Quadratic law for taking into account radiobiological effectiveness of an ion beam. Then, one can determine for instance radiobiological quantities induced by ion beam, by expressing them as functions of such linearly-superposable quantities.

Preferably, step b) of the method of the invention aims at determining several distributions of several linearly-superposable quantities, one or more of said linearly-superposable quantities being chosen among: dose, mean dose per unit fluence, mean track fluence per primary, mean energy transfer density per primary, mean dose-weighted energy transfer density per primary, average number of lethal events per primary depending on $\alpha$, square root of average number of lethal event per primary depending on $\beta$.

Preferably, the ion beamlets of step c) have different energy distributions. This is a simple way for approximating an energy distribution of the ion beam. It is also well-adapted when the energy distribution is a Gaussian energy distribution. Such an approximation provides an accurate modeling of a resulting effectiveness of an ion beam in a volume. Preferably, said different energy distributions of the ion beamlets are Dirac functions.

Preferably, said weighted superposition of step e) is performed in two times such that:
a partial solution is first computed by performing a first partial weighted superposition, and such that
a second partial weighted superposition using said partial solution is thereafter performed.

According to this preferred embodiment, a first partial weighted superposition can be carried out in advance, preferably offline (for instance during commissioning of the used ion beam line), reducing the amount of patient-specific computations. Longitudinal (or energy) weighted superposition is preferably performed offline.

Preferably, the reference ion beamlet(s) is (are) infinitesimal reference ion beamlet(s) having zero transverse spot size and no energy dispersion. More preferably, the reference ion beamlet(s) is (are) quasi-infinitesimal reference ion beamlet(s) having a spot size ranging between 0.1 mm and 0.3 mm (value of a transversal sigma) with a still more preferred value equal to 0.2 mm.

Preferably, the number of ion beamlets of step c) is comprised between 5 and 100. More preferably, the number of ion beamlets of step c) is comprised between 10 and 50, and is still more preferably equal to 20.

According to a second aspect, the invention relates to a device or Dose Engine Kernel (DEK) (or dose engine device or dose engine system) for computing in a volume physical and/or radiobiological quantities induced by an ion beam entering said volume, said device comprising:
pre-processing means configured for providing a reference ion beamlet representing an elementary ion beam;
pre-processing means configured for determining in a phantom a distribution of a linearly-superposable quantity representing a linearly-superposable effect induced by said reference ion beamlet entering said phantom;
pre-processing means configured for approximating said ion beam as a weighted superposition of ion beamlets,
i) one of said ion beamlets being said roto-translated ion beamlet that is obtained by applying to said reference ion beamlet a roto-translation operation, a roto-translation operation comprising an operation of rotation and/or translation,
ii) said weighted superposition comprising weight coefficients (preferably determined from a discretization of a phase space of said ion beam);
pre-processing means configured for roto-translating said distribution of a linearly-superposable quantity with said roto-translation operation, for obtaining a roto-translated distribution of same linearly-superposable quantity;
processing means configured for performing a weighted superposition comprising said roto-translated distribution and said weight coefficients, for obtaining said physical or radiobiological quantity.

Preferably, the device or DEK of the invention further comprises saving means for storing the linearly-superposable quantity induced by the reference ion beamlet in said phantom in a library. An example of saving means is a hard disk drive. An example of a library is a database.

SHORT DESCRIPTION OF THE DRAWINGS

These and further aspects of the invention will be explained in greater detail by way of examples and with reference to the accompanying drawings in which.

The drawings of the figures are neither drawn to scale nor proportioned. Generally, identical components are denoted by the same reference numerals in the figures.

DETAILED DESCRIPTION OF PREFERRED EMBODIMENTS

The method of the invention allows computing in a volume global quantities induced by an ion beam 10 entering said volume. The volume is part of a patient body for instance. Preferably, volume is a tumour. The ion beam 10 is preferably a beam of protons. More preferably, ion beam 10 is a beam of other ions such as carbon ions. Ion beam 10 could also be a beam of helium, lithium, or oxygen ions. Ion beam 10 is preferably a scanned pencil beam (for instance thanks to the use of scanning magnets). All types of source system that are known by the one skilled in the art can be used for generating the ion beam 10. Such a source system preferably comprises an accelerator of particles, such as a cyclotron, a beamline to transport the accelerated particles/ions, and a control system to control the accelerator and the beamline.

Physical and/or radiobiological quantities refer to global quantities or effects induced by the ion beam 10 in the volume. Examples of such global quantities or effects are the dose, D, track-averaged LET, $\langle \text{LET} \rangle$, dose-averaged LET, $\langle \text{LET} \rangle_D$, and survival, S. These terms are known by the one skilled in the art.

The method of the invention comprises different steps. First, one has to provide one or more reference ion beamlets. Then, one or more distributions of one or more linearly-superposable quantities are determined in a phantom, a linearly-superposable quantity representing a linearly-superposable effect induced by a reference ion beamlet. These one or more distributions of one or more linearly-superposable quantities are preferably stored in a database. Thereafter, the ion beam 10 is approximated as a weighted superposition of ion beamlets 15. At least one of said ion beamlets 15 is a roto-translated ion beamlet that is obtained by applying a roto-translation operation to a reference ion beamlet. Said weighted superposition comprises weight coefficients that are preferably determined from a discretization of a phase space of the ion beam 10. The roto-translation operations that have been applied to the reference ion beamlet(s) for obtaining the roto-translated ion beamlet(s) are then applied to the one or more distributions of one or more linearly-superposable quantities determined previously for obtaining corresponding roto-translated distributions of one or more linearly-superposable quantities. Last, a weighted superposition comprising said one or more roto-translated distributions of one or more linearly-superposable quantities and said weight coefficients is performed for obtaining said physical or radiobiological quantity. These different steps are now detailed according to preferred embodiments.

General Approach of the Method of the Invention: Use of a Set of Ion Beamlets 15 for Modelling a Ion Beam 10.

Figure 1:
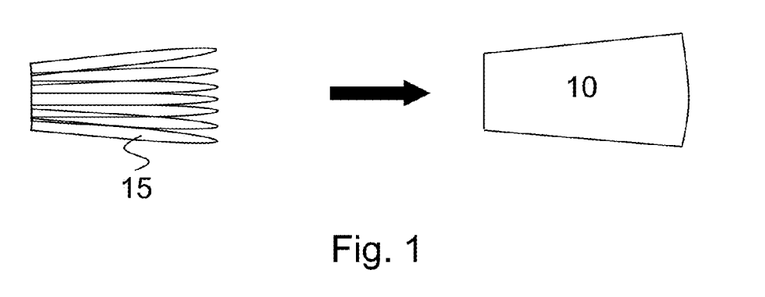
FIG. 1 shows a visual representation of a superposition of ion beamlets.

Every ion beam 10 can be modelled as composed of sub-units called ion beamlets 15 that are obtained by dividing said ion beam 10 in groups of ions. Ion beamlets 15 may be of dimensions comparable to ion beam 10, or very small, in the limit coincident with single particles, single ions. If the effect of interaction of individual ion beamlets 15 with a volume is known, then one can compute a total or global effect induced by an ion beam 10 by superpositing the separate ion beamlets effects, as long as the considered global effect is linear. This problem can be greatly simplified if another point of view is considered. Suppose to know the average effect of the interaction of a very small ion beamlet 15 with a representative homogeneous material. Then the average effect of whatever extended ion beam 10 on this material could be approximated with a superposition of opportunely weighted and effective replicas of effects induced by such ion beamlets 15. The smaller the used ion beamlet 15, the better the ion beam 10 reproduction. It is similar to what happens in building, where, once solved the problem of creating the basic brick (that is to know the ion beamlet effectiveness), it is possible to superpose several of them to build different constructions (that are the different effects of an ion beam 10 that is approximated by a superposition of ion beamlets 15). FIG. 1 schematically shows how several ion beamlets 15 can be combined or superposed for building an ion beam 10.

In what follows, linearly-superposable quantities are denoted by $\xi$. Linearly-superposable means linear with respect to intensity (or number of particles) of an ion beam 10 that induces such linearly-superposable quantities. Intensity is a term known by the one skilled in the art. Preferably, linearly-superposable quantities, $\xi$, are also intensive: this means not propotional to the volume considered to evaluate them.

General approach of the method of the invention is as follows. Assume that one aims at determining a linear quantity $\xi$ representing a linear effect induced by an ion beam 10 in a volume. If one knows linearly-superposable quantities, $\xi_i$, induced by ion beamlets 15, said linear quantity $\xi$ induced by the ion beam 10 can be approximated by using the following equation:

$$\xi = \sum_{i=1}^{M} \xi_i \varphi_i \quad \text{(Eq. 1):}$$

where $\varphi_i$ (i=1, . . . , M) represent weight coefficients, and where M is a number of ion beamlets 15 that are superposed for approximating said ion beam 10. Equation (Eq. 1) is a simplified expression but it can serve as an academic explanation of the global approach of the method of the invention. The method of the invention can be used for computing global intensive or extensive quantities that are not linear or not linearly-superposable provided such global intensive or extensive quantities can be expressed in terms of a function comprising linearly-superposable quantities $\xi$ or $\xi_i$. Examples of such global quantities that are not linear are given below.

First step of the method the invention (step a)) is to provide one or more reference ion beamlets, each of them being defined as an elementary ion beam. Preferably, each reference ion beamlet has a different minor phase space when there are several reference ion beamlets. The term 'minor' is used for differentiating the phase spaces of the (reference) ion beamlets from the phase space of the ion beam 10. The notion of phase space is known by the one skilled in the art and is explained below (see section entitled 'Modelling of ion beam 10 in air'). Preferably, each minor phase space comprises a longitudinal part (or a longitudinal phase space or an energy-related phase space), and a transversal part (or a transversal phase space). Preferably, each reference ion beamlet is characterized by a different energy distribution or a different longitudinal phase space when there are several reference ion beamlets. More preferably, the energy distribution of each reference ion beamlet is equivalently or less extended in energy than the energy distribution of the ion beam 10. Still more preferably, each reference ion beamlet has a well-defined energy, and each well-defined energy of each reference ion beamlet is different. This enables dealing with ion beams 10 presenting extended beam-energy spectra. Then, the energy step between the different well-defined energies of the different reference ion beamlets is preferably comprised between 5 and 10 MeV/u.

Preferably, the reference ion beamlet(s) is (are) characterized by a transversal spot size that is equal to or smaller than the transversal spot size of the ion beam 10. More preferably, the reference ion beamlet(s) is (are) infinitesimal which means that it has zero transversal spot size and no energy dispersion. Still more preferably, each reference ion beamlet has a small but finite size of around 0.2 mm transversal sigma (spot size). Then, subsequent superposition of different ion beamlets is easier.

Examples of linearly-superposable quantities induced by reference ion beamlets, and expressions of global quantities/effects (or physical and/or radiobiological quantities) in terms of such linearly-superposable quantities. Step b) of the method of the invention relates to determining in a phantom 60, for instance in a water phantom, a linearly-superposable quantity induced by the reference ion beamlet of step a) entering said phantom 60, preferably along a direction substantially perpendicular to a boundary surface of the phantom 60. The word 'substantially' means that the angle between main direction of reference ion beamlets and a boundary surface of the phantom 60 is comprised between 70° and 110°, and more preferably between 80° and 100°. Still more preferably, the angle between main direction of reference ion beamlets and a boundary surface of the phantom 60 is equal to 90°. Here below, examples of linearly-superposable quantities induced by reference ion beamlets in a phantom 60 are presented. This presentation relates to a preferred embodiment where said linearly-superposable quantities are determined from calculations. More specifically, this presentation relates to a preferred embodiment where said linearly-superposable quantities are determined with a numerical method that uses Monte Carlo simulations. However, same reasoning holds if linearly-superposable quantities were determined following another method, in particular if linearly-superposable quantities were determined experimentally, analytically, or from interpolation operations applied to linearly-superposable quantities obtained from simulations for instance.

Dose is an intensive and linear entity. It is derived by cumulating the energy depositions from different tracks, separated in slices and radial crowns, and by normalizing the result by the mass of the considered volumes and by the number of primary events. For each ion beamlet i, the mean dose per unit fluence in function of initial energy and of the position within the phantom 60 can be obtained by Monte Carlo simulations, that is $\langle D \rangle_i^0$ or $\langle D \rangle_i^0$ (E,z,r). Superscript ° is used for designating 'per primary event'. 'Per primary' or 'per primary event' means for each initial event of an ion impinging on the considered body. The term 'track' is known by the one skilled in the art. It is used in particle physics to designate an ionizing (usually charged) particle progressing in a medium. This term is widely used in Monte Carlo codes and in radiobiology. Radial coordinates, (z,r), are referenced to an ion beamlet 15 or to a reference ion beamlet. Hence, z coordinate is parallel to the direction of propagation of an ion beamlet 15 (or of a reference ion beamlet), whereas r coordinate is an associated perpendicular radial coordinate.

Dose (example of a global quantity that is in this case a linearly-superposable quantity, ξ) related to the composition of M ion beamlets 15 is then given by the following equation:

$$D = \Sigma_{i=1}^{M} \langle D \rangle_i^0 \varphi_i \quad \text{(Eq. 2)}$$

Preferably, each ion beamlet i 15 has a well-defined energy, $E^i$.

There are two quantities of interest for LET (Linear Energy Transfer). First one that is given by following equation is a track-averaged LET:

$$\langle LET \rangle = \frac{\sum_{j=1}^{N} LET_j}{N} \quad \text{(Eq. 3)}$$

where N is a total number of tracks traversing a considered area A. Second quantity of interest for LET that is given by following equation is a dose-averaged LET:

$$\langle LET \rangle_D = \frac{\sum_{j=1}^{N} LET_j^2}{\sum_{j=1}^{N} LET_j}. \quad \text{(Eq. 4)}$$

These two quantities, $\langle LET \rangle$ and $\langle LET \rangle_D$ are not linearly-superposable quantities but are nevertheless physical quantities (or global quantities/effects) that can be determined by the method of the invention. They can indeed be expressed as functions of linear combinations of the following linearly-superposable quantities: mean track fluence per primary, $\langle f \rangle_i^0$, mean energy transfer density per primary, $\langle \rho_e \rangle_i^0$, and mean dose-weighted energy transfer density per primary, $\langle \rho_{e^2} \rangle_i^0$. Expressions of these three linearly-superposable quantities are given by the following equations:

$$\langle f \rangle^0 = \frac{N}{N_P A} \quad \text{(Eq. 5)}$$

$$\langle \rho_e \rangle^0 = \frac{\sum_{j=1}^{N} LET_j}{N_P A} \quad \text{(Eq. 6)}$$

$$\langle \rho_{e^2} \rangle^0 = \frac{\sum_{j=1}^{N} LET_j^2}{N_P A} \quad \text{(Eq. 7)}$$

where $N_P$ is a total number of simulated primary events. Finally, $\langle LET \rangle$ and $\langle LET \rangle_D$ can be expressed as a function of weighted superpositions of linearly-superposable quantities induced by M ion beamlets 15:

$$\langle LET \rangle = \frac{\sum_{i=1}^{M} \langle \rho_e \rangle_i^0 \phi_i}{\sum_{i=1}^{M} \langle f \rangle_i^0 \phi_i} \quad \text{(Eq. 8)}$$

$$\langle LET \rangle_D = \frac{\sum_{i=1}^{M} \langle \rho_{e^2} \rangle_i^0 \phi_i}{\sum_{i=1}^{M} \langle \rho_e \rangle_i^0 \phi_i} \quad \text{(Eq. 9)}$$

where $\varphi_i$ (i=1, . . . , M) represent weight coefficients, and where M is a number of ion beamlets 15 used for approximating said ion beam 10.

Radiobiological quantities provide information about the effectiveness in cell killing associated to the different positions within an ion beam 10 interaction region. Radiobiological effect varies not only in virtue of changes in the local particles spectra, but also depending on the biological properties of the irradiated material. Radiobiological effectiveness is described by means of a clonogenic survival curve S(D), that gives the probability S for a cell of a specified population to maintain its normal duplication capability after having been irradiated with a dose D of a certain ionization field. Experimental studies show that survival curves can usually be very well described with an exponential function of the following type:

$$S(D) = e^{-\langle L \rangle} = e^{-\alpha D - \beta D^2} \quad \text{(Eq. 10)}$$

that is called Linear-Quadratic (LQ) parameterization.

The presence of the exponential function can be explained by the fact that survival is the lacking of irradiation-produced lethal events, together with the assumption that the number of lethal events is L Poisson distributed. The two parameters, α and β, which respectively regulate the linear and the quadratic dose dependence at the exponent, can be used to concisely describe a survival curve. These two parameters can be estimated by applying radiobiological models. The Local Effect Model (LEM) and the Microdosimetric Kinetic Model (MKM) are so far the most employed models in the clinical practice. These models are known by the one skilled in the art. These two models are able to provide an estimate for α and β related to an ion irradiation, starting from the information of the field composition and the corresponding $\alpha_x$ and β, parameters for conventional X-ray irradiation. With these tools it is thus possible to process the tracks information recorded from the Monte Carlo to generate three-dimensional distributions of α and β for the different quasi-infinitesimal ion beamlets 15 on the different tissues. However, neither α nor β are linearly-superposable quantities. When M irradiation fields are superposed, the commonly accepted rule for the computation of the global LQ parameters is the one proposed by Zaider and Rossi 1980 (Rad. Res. 83, 732-739), which consists in the following dose-weighted averaged quantities:

$$\alpha = \frac{\sum_{i=1}^{M} \alpha_i D_i}{\sum_{i=1}^{M} D_i}, \quad \text{(Eq. 11)}$$

$$\sqrt{\beta} = \frac{\sum_{i=1}^{M} \sqrt{\beta_i} D_i}{\sum_{i=1}^{M} D_i}. \quad \text{(Eq. 12)}$$

This suggests that the sought linearly-superposable quantities are the average number of lethal events per primary depending on $\alpha$, $$\langle L_\alpha \rangle^o = \alpha \langle D \rangle^o \quad \text{(Eq. 13),}$$

and the square root of the average number of lethal events per primary depending on $\beta$, $$\sqrt{\langle L_\beta \rangle^o} = \sqrt{\beta} \langle D \rangle^o \quad \text{(Eq. 14).}$$

In this way, the weighted superposition of M ion beamlets 15 can be written as:

$$\langle L_\alpha \rangle = \Sigma_{i=1}^{M} \langle L_\alpha \rangle_i^o \varphi_i \quad \text{(Eq. 15),}$$

$$\sqrt{\langle L_\beta \rangle} = \Sigma_{i=1}^{M} \sqrt{\langle L_\beta \rangle_i^o} \varphi_i \quad \text{(Eq. 16).}$$

So, the sought linearly-superposable quantities are $\langle L_\alpha \rangle^o$ (E,z,r) and $\sqrt{\langle L\beta \rangle^o}$ (E,z,r). These linearly-superposable quantities can be determined for different reference ion beamlets i 15, having different well-defined energy, $E_i$. Then, the following linearly-superposable quantities are determined in step b) for each reference ion beamlet number i 15: $\langle L_\alpha \rangle_i^o = \langle L_\alpha \rangle^o$ (E z, r), and $\langle L_\beta \rangle_i^o = \sqrt{\langle L_\beta \rangle^o}(E_i, z, r)$.

Global radiobiological quantities (that are not linearly-superposable in general) such as survival and RBE-weighted dose can be computed from $\langle L_\alpha \rangle$ and $\sqrt{\langle L_\beta \rangle}$ that are given by equations (Eq. 15) and (Eq. 16) (RBE means Relative Biological Effectiveness). For instance, survival is given by:

$$S = e^{-\langle L \rangle} \quad \text{(Eq. 17)}$$

where $$\langle L \rangle = \langle L_\alpha \rangle + \langle L_\beta \rangle \otimes \quad \text{(Eq. 18).}$$

RBE-weighted dose, $D_{RBE}$, is the X-ray dose, $D_x$, that produces same survival probability as an ion beam 10, that is:

$$D_{RBE} = \frac{-\alpha_x + \sqrt{\alpha_x^2 + 4\beta_x \langle L \rangle}}{2\beta_x}. \quad \text{(Eq. 19)}$$

Therefore, one or more of the following linearly-superposable quantities, $\langle f \rangle_i^o$, $\langle \rho_e \rangle_i^o$, $\langle \rho_{e^2} \rangle_i^o$, $\langle L_\alpha \rangle_i^o$, and $\langle L_\beta \rangle_i^o$, are preferably determined in step b). Preferably, these chosen quantities are determined by using Monte Carlo simulations. More preferably, a Fluka package that is known by the one skilled in the art is used for carrying out Monte Carlo simulations.

Preferably, the linearly-superposable quantities are computed in a water phantom that is divided in slices positioned along the reference ion beamlet path. Preferably, about one hundred of such slices are generated. Preferably, these slices have a thickness of around 10 µm. More preferably, such slices are more densely located near the Bragg peaks.

Thereafter, the linearly-superposable quantities that are determined in step b) are preferably saved in a database. In this manner, the linearly-superposable quantities can be computed in advance for a later use.

Modelling of the Ion Beam 10 in Air.

Step c) of the method of the invention relates to approximating the ion beam 10 as a weighted superposition of ion beamlets 15. At least one (preferably all) ion beamlet 15 is a roto-translated ion beamlet obtained by applying a roto-translation operation to a reference ion beamlet. The weighted superposition comprises weight coefficients for determining the importance, the weight of each ion beamlet 15 for approximating the ion beam 10. The roto-translation operation(s) applied to the used reference ion beamlet(s) allow(s) approximating the geometrical properties of the ion beam 10 such as its direction of penetration in the volume for instance. Preferably, the weight coefficients are determined from a phase space of the ion beam 10. This allows taking into account properties of the ion beam 10 before it enters the volume, and in particular its propagation properties. These properties are beam-delivery-system specific. We now explain how the notion of phase space of an ion beam 10 can be used for modelling it in air. A detailed description including decomposition in longitudinal and transversal phase spaces, and the introduction of a water-equivalent thickness (WET) distribution for the longitudinal phase space is presented below. Such a complete description is useful for some preferred embodiments of the method of the invention. However, simpler or more general expressions of phase space of an ion beam 10 could be used for the method of the invention. According to another preferred embodiment, no knowledge of the phase space of the ion beam is needed.

The specificities of an ion beam 10 (or beam line) are manifested in the characteristics of the produced smaller beams around the isocenter, in the absence of a volume. The term 'isocenter' is known by the one skilled in the art. It is a point in space through which a central smaller beam of radiation of said ion beam 10 passes. Generally, said smaller beams forming the ion beam 10 evolve during their propagation around the isocenter and along the main propagation path due to interactions with air molecules and to redistributions of ions according to their different directions. These evolutions have to be taken into account. An approach based on beam optics theory is proposed for describing the evolution of the ion beam 10 along its main propagation path. Beam optics theory is known by the one skilled in the art, see for instance p xi of "Beam and Fiber Optics" by JA Arnaud. This theory provides a mathematical description of the evolution of the beam phase space. The term beam phase space is known by the one skilled in the art, see for instance p 42 of "Modern Developments in X-Ray and Neutron Optics", by A. Erko et al. According to this approach, all the particles (or ions) that constitute an ion beam 10 are supposed to be identical and independent.

Time-related aspects of the propagation of an ion beam 10 are not of interest in the present case: it is sufficient to consider probability distributions. Phase space is preferably decomposed in two independent phase spaces:

one for the energy, $f_L$, and the other for the spatial attributes (positions and directions).

By taking the convention that Z axis is coincident with main propagation path (or main axis 11) of the ion beam 10, the spatial part of the beam phase space can further be split along X and Y. Therefore, the time-independent beam phase space, f, at a given $z=z^*$ can be written as follows:

$$f = g(x, u_x)|_{z=z^*} \cdot g(y, u_y)|_{z=z^*} \cdot f_L|_{z=z^*}. \quad \text{(Eq. 20)}$$

$u_x$ and $u_y$ represent X and Y coordinates of ions directions u. Preferably, $g(x, u_x)$ and $g(y, u_y)$ are Gaussian distributions. A change of variables such that $$\vec{u} = K(x', y', 1) \quad \text{(Eq. 21)},$$

leads a rewriting of equation (Eq. 20) according to the following equation:

$$f = g(x, x')|_{z=z^*} \cdot g(y, y')|_{z=z^*} \cdot f_L|_{z=z^*}. \quad \text{(Eq. 22)}$$

Dispersion in the beam energy spectra is connected with the longitudinal width of the Bragg peak produced in the medium; therefore, $f_L$ is preferably named longitudinal phase space. Spatial part of equation (Eq. 22), $g(x, x')|_{z=z^*} \cdot g(y, y')|_{z=z^*}$, mainly affects the lateral spread of the peak and is therefore preferably named transverse phase space.

Longitudinal Phase Space

Longitudinal phase space, $f_L$, can be the result of the combination of different effects: energy spread due to the source of beam of particles (synchrotron, cyclotron for instance), presence of elements along the main propagation path, . . . . Preferably, longitudinal phase space is given by:

$$f_L = w(z) \otimes g(E), \quad \text{(Eq. 23)}$$

where w(z) represents a probability distribution of Water-Equivalent Thicknesses (WETs) (also named Water-Equivalent Thickness (WET) distribution) traversed by the different ions of the ion beam 10, and where g(E) is an energy distribution, preferably a Gaussian energy distribution, expressing a spread in energy. E is the energy of the ions. Monoenergetic case is obtained as a particular case of such a Gaussian energy distribution, g(E), with zero standard deviation. Monoenergetic case can also be modelled by using a Dirac distribution for g(E). Details of w(z) and g(E) distributions are preferably determined during the commissioning of a beam line. Then, w(z) and g(E) distributions are preferably fixed by adjusting them to best reproduce depth-dose profiles that are measured during said commissioning.

In another preferred embodiment, longitudinal phase space is given by:

$$f_L = g(E), \quad \text{(Eq. 24)}$$

In another preferred embodiment, longitudinal phase space is given by:

$$f_L = w(z), \quad \text{(Eq. 25)}.$$

Transversal Phase Space

According to a preferred embodiment, the inventors propose the following expression for the transversal phase space along X:

$$g(x, x'; z) = g(x; \mu_x(z, x'), \sigma_x(z_s)) g(x'; \mu_{x'} = 0, \sigma_{x'}) \quad \text{(Eq. 26)}$$

where $$\mu_x(z, x') = (z - z_s) x' \quad \text{(Eq. 27)}$$

with $z_s$ being the virtual source position, that is the location at which the ion beam 10 is at its maximum convergence (minimum $\sigma_x$).

$g(x'; \mu_{x'} = 0, \sigma_{x'})$ is preferably a Gaussian distribution that stays constant during the propagation of the ion beam 10 as it does not depend on z. $\sigma_{x'}$ is the divergence along X of the ion beam 10. Preferably, $\sigma_{x'}$ is considered constant: this corresponds to independent ions propagating in vacuum. As $\mu_{x'} = 0$, one can determine $g(x'; \mu_{x'} = 0, \sigma_{x'})$ if $\sigma_{x'}$ is provided.

$g(x; \mu_x(z, x'), \sigma_x(z_s))$ is preferably a Gaussian distribution. For determining $g(x; \mu_x(z, x'), \sigma_x(z_s))$, the inventors propose the following procedure.

One first needs to determine $z_s$. The inventors propose to use the following equation:

$$z_s = \tilde{z} - \rho_{xx'}(\tilde{z}) \frac{\sigma_x(\tilde{z})}{\sigma_{x'}}, \quad \text{(Eq. 28)}$$

where:

$\tilde{z}$ is a given position along the main propagation path of the ion beam 10 (chosen by the user, thus known), $\rho_{xx'}(\tilde{z})$ represents a correlation at said given position $\tilde{z}$. More precisely, $\rho_{xx'}(\tilde{z})$ represents a statistical correlation between x and x' coordinates of a set of ions at a certain position along z. Such a correlation is known by the one skilled in the art.

$\sigma_x(\tilde{z})$ represents a spot size of the ion beam 10 at said given position $\tilde{z}$ and can be measured.

$\sigma_{x'}$ is the divergence along X of the ion beam 10 (see above).

Hence, if one knows $\sigma_{x'}$, $\sigma_x(\tilde{z})$, and $\rho_{xx'}(\tilde{z})$, $z_{29}$ can be determined and therefore also $\mu_x(z, x')$ by using equation (Eq. 27). From this equation, one can learn that during the propagation of the ion beam 10, the mean values of the phase space profiles along x are shifting of different amounts, according to their respective x' positions.

It remains $\sigma_x(z_s)$ for determining $g(x; \mu_x(z, x'), \sigma_x(z_s))$. Preferably, $\sigma_x(z_s)$, $\sigma_{x'}$, $\sigma_x(\tilde{z})$, and $\rho_{xx'}(\tilde{z})$ are determined at a same time, using them as free parameters for fitting an experimental phase space evolution with the following equation:

$$\sigma_x(z) = \sqrt{\sigma_x^2(z_s) + (z - z_s)^2 \sigma_{x'}^2} \quad \text{(Eq. 29)}$$

where (Eq. 28) is used for expressing $z_s$ as a function of $\tilde{z}$, $\rho_{xx'}(\tilde{z})$, $\sigma_x(\tilde{z})$, and $\sigma_{x'}$. More precisely, experimental characterization of $\sigma_x(z)$ obtained by measuring a, at different positions around the isocenter, for different energies and different beamline configurations is fitted with (Eq. 29) and (Eq. 28) is used. Same reasoning preferably applies for the transversal phase space along Y.

Discretization and Superposition

As explained previously, global effect induced by an ion beam 10 may be obtained from the knowledge of the effect of a smaller reference ion beamlet, through an approximate reproduction of said ion beam 10 with an opportune weighted superposition of effective replicas of such reference ion beamlets. Said effective replicas of said reference ion beamlets are named ion beamlets 15. The purpose is to find a good discretization of the phase space of the ion beam 10 where it enters the volume, that would allow obtaining a good evaluation of the ion beam 10 effectiveness (within a few percents) superposing a manageable number (few tens) of ion beamlets 15. Using a description of phase space as the one described in previous paragraphs (that means a description employing Gaussians probability distributions) allows having such a good evaluation more easily.

Discretization of the Longitudinal Phase Space

Distribution g(E) of equation (Eq. 23) is preferably approximated as weighted sum of $N_E$ monoenergetic ion beamlets 15:

$$g(E) \cong \sum_{l=-\frac{N_E-1}{2}}^{l=\frac{N_E-1}{2}} g_{E,l} \delta(E - (\mu_E + l\Delta E)). \quad (Eq.\ 30)$$

$\delta$ represents a Dirac function; $\Delta E$ is the spacing between two Dirac functions, and $g_{E,l}$ is the weight assigned to the l-th beamlet. Preferably, $g_{E,l}$ is determined by using the following equation:

$$g_{E,l} = \int_{\mu_E + (l-1/2)\Delta E}^{\mu_E + (l+1/2)\Delta E} g(E; \mu_E, \sigma_E) dE \quad (Eq.\ 31),$$

where g(E) or g(E; $\mu_E$, $\sigma_E$) is known and is preferably determined during commissioning.

Preferably, $\Delta E$ is comprised between 0.5 and 2 MeV/u. More preferably, $\Delta E = 1$ MeV/u. Preferably, $N_E$ is comprised between 5 and 20. More preferably, $N_E = 10$.

Preferably, w(z) distribution entering equation (Eq. 23) is approximated by a weighted sum of $N_z$ shifted ion beamlets 15 according to the following equation:

$$w_z = \sum_{k=0}^{N_z - 1} w_k \delta(z - k \Delta z). \quad (Eq.\ 32)$$

Preferably, w(z) distribution is a continuous function. Then an equation equivalent to (Eq. 31) can be used for determining $w_k$ coefficients. More preferably, w(z) distribution is directly expressed as a discrete function. Then, the $w_k$ coefficients correspond to the different values of said w(z) distribution at the different $\Delta z$ shifts. Preferably, $N_z$ is comprised between 7 and 10. Such preferred values for $N_z$ are preferably used if a passive range modulator such as a ripple filter is used. More preferably, $N_z$ is equal to one for example when no passive range modulator is used. Preferably, $\Delta z$ is comprised between 0.1 and 1 mm.

Discretization of the Transversal Phase Space

Distribution g (x'; $\mu_{x'} = 0$, $\sigma_{x'}$) entering equation (Eq. 26) is preferably approximated by a weighted sum of $N_{x'}$ Dirac functions:

$$g(x'; \mu_{x'} = 0, \sigma_{x'}) \cong \sum_{i'=-\frac{N_{x'}-1}{2}}^{\frac{N_{x'}-1}{2}} g_{x',i'} \delta(x' - i'\Delta x') \quad (Eq.\ 33)$$

where weight coefficient $g_{x', i'}$ is preferably given by:

$$g_{x',i'} = \int_{(i'-1/2)\Delta x'}^{(i'+1/2)\Delta x'} g(x', \mu_{x'} = 0, \sigma_{x'}) dx' \quad (Eq.\ 34).$$

Then, equation (Eq. 26) can be rewritten as:

$$g(x, x'; z) \cong \quad (Eq.\ 35)$$

$$\sum_{i'=-\frac{N_{x'}-1}{2}}^{\frac{N_{x'}-1}{2}} g_{x',i'} \delta(x' - i'\Delta x') g(x; \mu_x = (z - z_s)x', \sigma_x(z_s))$$

Hence, the ion beam 10 is preferably decomposed in $N_{x'}$ zero-divergence ion beamlets 15 as $\sigma_x$ of each ion beamlet 15 does not change during the beam propagation. Each ion beamlet 15 has a $\sigma_x(z_s)$ spot size, and is opportunely oriented and weighted. $\sigma_x$ of the composite beam obtained from superposition changes in a general case due to relative mutual displacement of the ion beamlets 15. Preferably, $N_{x'}$ is comprised between 3 and 7, preferably when ion beam 10 is divergent along X. More preferably, $N_{x'}$ is equal to 1, preferably when ion beam 10 is not divergent along X. Preferably, $$\Delta x' \leq \frac{\sigma_x(z_s)}{\max_{l_z}(|z - z_s|)} \quad (Eq.\ 36^*)$$

where $I_z$ is a set of z positions where the ion beam 10 intersects the volume.

Preferably, g(x; $\mu_x$, $\sigma_x(z_s)$) entering equation (Eq. 35) is given by:

$$g(x; \mu_x, \sigma_x(z_s)) \cong \sum_{i=-\frac{N_x-1}{2}}^{\frac{N_x-1}{2}} g_{x,i} g(x; \mu_x + i\Delta x, \tilde{\sigma}_x), \quad (Eq.\ 36)$$

where $$g_{x,i} = \int_{(i-1/2)\Delta x}^{(i+1/2)\Delta x} g(x; 0; \hat{\sigma}_x) dx. \quad (Eq.\ 37)$$

Distribution g(x; 0; $\hat{\sigma}_x$) is preferably a Gaussian distribution where:

$$\hat{\sigma}_x = \sqrt{\sigma_x^2(z_s) - \tilde{\sigma}_x^2} \quad (Eq.\ 38)$$

where $\tilde{\sigma}_x$ is chosen by the user, and were $\sigma_x(z_s)$ can be determined following fitting procedure that has been detailed above for instance.

Preferably, $$\Delta x \leq \min\left(\tilde{\sigma}_x, \frac{\sigma_x(z_s)}{5}\right). \quad (Eq.\ 39)$$

Then, once $\tilde{\sigma}_x$ has been chosen by the user, $\Delta x$ can be determined by using inequality of equation (Eq. 39). Preferably, $N_x$ is comprised between 3 and 7. More preferably, $N_x = 1$, preferably when ion beam 10 is approximated as originating from a point-like source.

Then equation (Eq. 26) is preferably given by:

$$g(x, x'; z) \cong \sum_{i'=-\frac{N_{x'}-1}{2}}^{\frac{N_{x'}-1}{2}} g_{x',i'} \delta(x' - i'\Delta x') \quad (Eq.\ 40)$$

$$\sum_{i=-\frac{N_x-1}{2}}^{\frac{N_x-1}{2}} g_{x,i} g(x; \mu_x = (z - z_s)x' + i\Delta x, \tilde{\sigma}_x).$$

Figure 2:
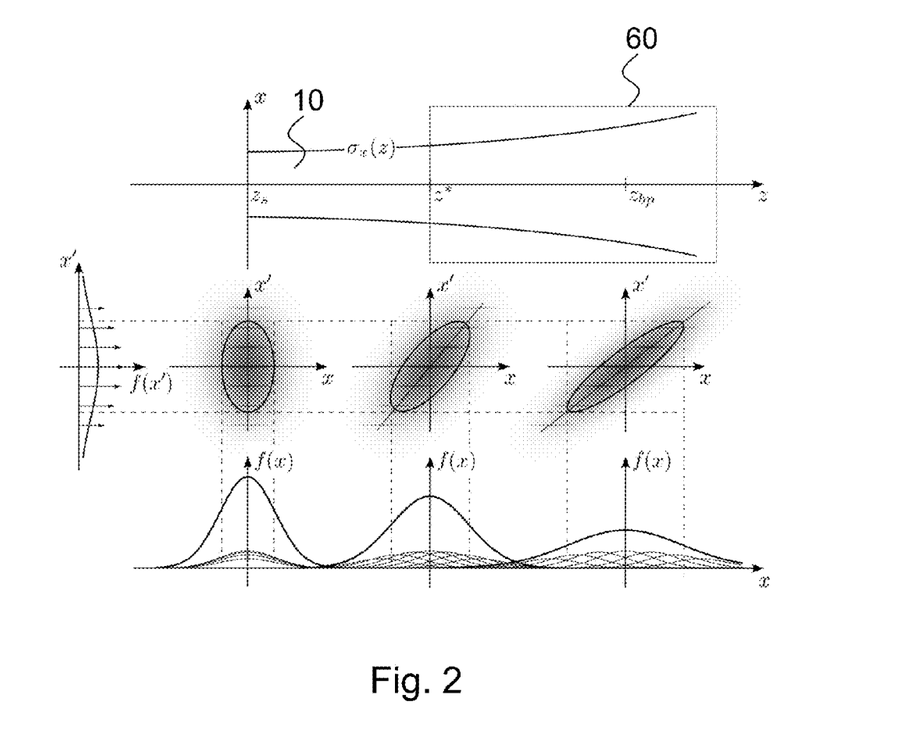
FIG. 2 illustrates an example of discretization of a transversal phase space along x and x' of an ion beam as it propagates and enters a phantom.

Therefore, for what concerns the discretization along x and x', the ion beam 10 is preferably divided in $N_{x'}$, $N_x$ identical, zero-divergence ion beamlets 15 having $\tilde{\sigma}_x$ as Gaussian spot size in air. The (i,i') ion beamlet 15 is centered at $x = (z - z_s)$ i'$\Delta x'$ + i $\Delta x$ and is characterized by a rate of displacement along x that is given by x'=i'$\Delta x'$. The discretization related to equation (Eq. 40) is illustrated in FIG. 2 whose upper part shows extension of the ion beam 10 along X, and its evolution as it enters a phantom 60 (z-axis represents main axis of propagation of the ion beam 10). Discretization along X' is achieved by summing $N_{x'}$ Dirac's deltas, and discretization along X is achieved by summing k Gaussian functions.

Same procedure as the one described above for discretization along x and x' can be followed for the discretization along y and y'.

Superposition of Linearly-Superposable Quantities.

From what has been explained above, there are preferably $N_E \times N_z \times N_x \times N_{x'} \times N_y \times N_{y'}$ ion beamlets 15 for approximating the ion beam 10. Preferably, each of said ion beamlets 15 is obtained from a reference ion beamlet of the set of reference ion beamlets that has been introduced in step a) to which a roto-translation operation is applied in order to approximate at best the ion beam 10. Depending on the phase space of the ion beam 10, on the chosen discretization and on the way of modeling the phase space, the number of ion beamlets 15 may change. For instance, when no WET distribution, w(z), is introduced in the modeling of the longitudinal phase space, the number of ion beamlets 15 is rather equal to $N_E \times N_x \times N_{x'} \times N_y \times N_{y'}$. Preferably, $N_E \times N_z \times N_x \times N_{x'} \times N_y \times N_{y'}$ is comprised between $2 \cdot 10^4$ and $10^6$. More preferably, $N_E \times N_z \times N_x \times N_{x'} \times N_y \times N_{y'}$ is comprised between 10 and 500. Still more preferably, $N_E \times N_z \times N_x \times N_{x'} \times N_y \times N_{y'}$ is equal to twenty.

Superposition is now presented in order to compute physical and/or radiobiological quantities representing effects induced by an ion beam 10 in a volume. Phantom's front face and entrance of the volume must be located at a same z=z* position along the main propagation path 11 of the ion beam 10. A global linear effect, $\xi(\vec{r})$, is computed in the following way.

Preferably, superposition according to the longitudinal phase space is first performed:

$$\xi(r, z) \cong \sum_{l=-\frac{N_E-1}{2}}^{+\frac{N_E-1}{2}} g_{E,l} \xi_{LUT}(\mu_E + l\Delta E, r, z) \quad \text{(Eq. 41)}$$

where $\xi_{LUT}$ represents a linearly-superposable quantity induced by a reference ion beamlet (see step b)). When introducing a WET distribution, w(z), previous equation (Eq. 41) is rather replaced by the following equation:

$$\xi(r, z) \cong \sum_{k=0}^{N_z} w_k \sum_{l=-\frac{N_E-1}{2}}^{+\frac{N_E-1}{2}} g_{E,l} \xi_{LUT}(\mu_E + l\Delta E, r, z + k\Delta z). \quad \text{(Eq. 42)}$$

Equations (Eq. 41) and (Eq. 42) are only correct when there is cylindrical symmetry. In order to deal with possible spot asymmetries, a carthesian representation must be adopted. By expressing:

$$z = \vec{u}_0 \cdot (\vec{r} - \vec{r}_0) \quad \text{(Eq. 43),}$$

$$r = |\vec{u}_0 \times (\vec{r} - \vec{r}_0)| \quad \text{(Eq. 44),}$$

where $\vec{r}_0$ and $\vec{u}_0$ respectively identify position and orientation of an ion beamlet 15 at a phantom entrance, and by making a superposition according to the transversal phase space, one can finally obtain the following equation:

$$\xi(\vec{r}) \cong \Sigma_{ii'jj'} g_{x,i} g_{x',i'} g_{y,j} g_{y',j'} \Sigma_l g_{E,l} \xi_{LUT}(\mu_E + l\Delta E, |\vec{u}_{0ij} \times (\vec{r} - \vec{r}_{0,ii'jj'})|, \vec{u}_{0,i'j'} \cdot (\vec{r} - \vec{r}_{0,ii'jj'})) \quad \text{(Eq. 45)}$$

when no WET distribution w(z) is introduced, and the following equation $$\xi(\vec{r}) \cong \Sigma_{ii'jj'} g_{x,i} g_{x',i'} g_{y,j} g_{y',j'} \Sigma_k w_k \Sigma_l g_{E,l} \xi_{LUT}(\mu_E + l\Delta E, |\vec{u}_{0ij} \times (\vec{r} - \vec{r}_{0,ii'jj'})|, \vec{u}_{0,i'j'} \cdot (\vec{r} - \vec{r}_{0,ii'jj'}) + k\Delta z) \quad \text{(Eq. 46)}$$

when a WET distribution w(z) is introduced in the longitudinal phase space. Expressions of weight coefficients, $g_{E,l}$, $w_k$, $g_{x,i}$, $g_{x',i'}$, $g_{y,j}$, $g_{y',j'}$, have been presented above. These weight coefficients are preferably determined from the phase space of the ion beam 10. Vector $\vec{r}_{0,ii'jj'}$ is given by the following equation:

$$\vec{r}_{0,ii'jj'} = ((z^* - z_{s,x})i'\Delta x' + i\Delta x, (z^* - z_{s,y})j'\Delta y' + j\Delta y, 0) \quad \text{(Eq. 47)}$$

where $z_{s,x}$ is given by equation (Eq. 28), and where $z_{s,y}$ is given by a corresponding equation in the (y, y') coordinates. Vector $\vec{u}_{0,i'j'}$ is given by the following equation:

$$\vec{u}_{0,i'j'} = \frac{1}{\sqrt{(i'\Delta x')^2 + (j'\Delta y')^2 + 1}} (i'\Delta x', j'\Delta y', 1). \quad \text{(Eq. 48)}$$

Hence, as it can be seen in equations (Eq. 45) and (Eq. 46), roto-translation operations are applied to the linearly-superposable quantities for expressing a global linear effect, $\xi$, in a global reference system $\vec{r} = (x, y, z)$. This is necessary as linearly-superposable quantities induced by the reference ion beamlets of step a), $\xi_{LUT}$, are generally determined, in step b), in a cylindrical reference system of each reference ion beamlet, (r, z).

Preferably, the method of the invention further comprises a step of determining a water equivalent path (WEP) mapping between path lengths of said ion beam 10 in said volume and path lengths of same ion beam 10 in said phantom 60 where said linearly-superposable quantities induced by the reference ion beamlets are determined. An infinitesimal path length of an ion beam in a certain material, $dl_m$, can be mapped to its water-equivalent $dl_w$ by the following equation:

$$dl_w = \frac{\rho_m s_m}{\rho_w s_w} dl_m \quad \text{(Eq. 49)}$$

where $S_m$ and $S_w$ represent mass stopping power respectively in said certain material and in water. Such mass stopping power quantities are known by the one skilled in the art. $\rho_m$ and $\rho_w$ are mass densities respectively in said certain material and in water. Total water-equivalent path length can be computed by integrating equation (Eq. 49). Alternatively, one could consider path lengths of a reference ion beamlet or of an ion beamlet for determining said water equivalent path (WEP) mapping. Three preferred embodiments of the method of the invention are presented below for applying a water equivalent path (WEP) mapping.

Figure 3:
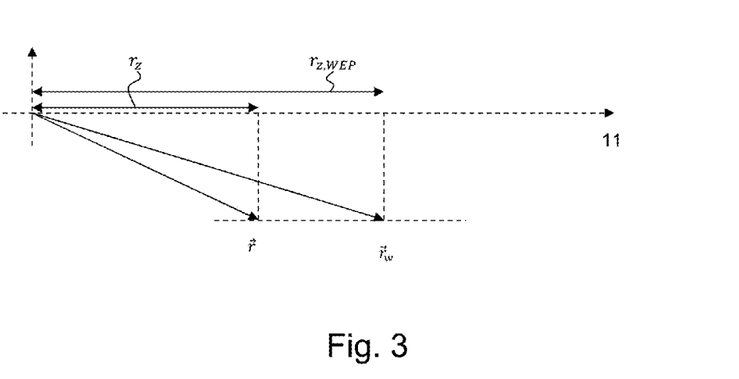
FIG. 3 illustrates a step of a preferred embodiment of the method of the invention using a water-equivalent path mapping.

According to a first preferred embodiment, this WEP mapping is applied to the physical and/or radiobiological quantities determined in step e), from the weighted superposition that involves the weight coefficients and the at least one roto-translated distribution. More precisely, water equivalent path lengths are attributed to each position in the volume, for instance by integrating equation (Eq. 49) if stopping powers are known. Every position $\vec{r}$ in the volume is rescaled in a coordinate system of the ion beam 10: projection of $\vec{r}$ on main axis 11 of the ion beam 10 is rescaled according to the water-equivalent path length and a water-equivalent position $\vec{r}_w$ is obtained. FIG. 3 illustrates this operation. Global linear quantity, $\xi$, that is determined as described above (weighted superposition using weight coefficients and linearly-superposable quantities, at least one of them being roto-translated) is in fact calculated at different $\vec{r}_w$ and each calculated linear quantity, $\xi(\vec{r}_w)$, is associated to a corresponding linear quantity, $\xi(\vec{r})$, in the volume. Hence, a global linear quantity, $\xi(\vec{r}_w)$ calculated from the linearly-superposable unitary quantities is longitudinally stretched according to inhomogeneities of the volume along main axis 11 of the ion beam 10 for obtaining $\xi(\vec{r})$. Preferably, a transversal stretching following same approach as for longitudinal stretching is also used.

According to a second preferred embodiment, the water equivalent path mapping is applied to the linearly-superposable quantity induced by the reference ion beamlet and determined in step b) before carrying out the weighted superposition of step e). Same approach as the one described in previous paragraph is followed for applying water equivalent path mapping to said linearly-superposable quantity. With this second preferred embodiment, each portion of the ion beam 10 is deformed according to a more local WEP mapping and a more faithful representation of the ion beam propagation can be achieved. Thereafter, weighted superposition is carried out as described previously on the WEP-scaled linearly-superposable quantities.

According to a third preferred embodiment, ion beam 10 is first divided in sub-beams, each sub-beam comprising a limited set of ion beamlets 15. Sub-global quantities or sub-global effects induced by said sub-beams are calculated for each sub-beam by using the weighted superposition approach that has been explained previously. Thereafter, water equivalent path mapping is applied so said sub-global quantities and finally another weighted superposition of such WEP-scaled sub-global quantities is achieved for getting the global quantity $\xi(\vec{r})$. This third preferred embodiment allows having a higher precision than first preferred embodiment while keeping the calculation time at a reasonable level. This third preferred embodiment indeed needs less computational resources than second preferred embodiment described in previous paragraph.

According to a second aspect, the invention relates to a device 100 or Dose Engine Kernel (DEK) 100, or dose engine system 100, or dose engine device 100. This device 100 is able to perform the method of the invention and all its preferred embodiments. As a general remark, all the essential and preferred technical features that have been described for the method of the invention apply to the device 100 when applicable, mutatis mutandis. Preferably, device 100 is a personal computer. More preferably, device 100 is a computing device able to interact with a treatment planning system. Sill more preferably, device 100 is a component of a treatment planning system. Device 100 can also refer to different computing modules/units that do not form part of a same computing system.

Figure 4:
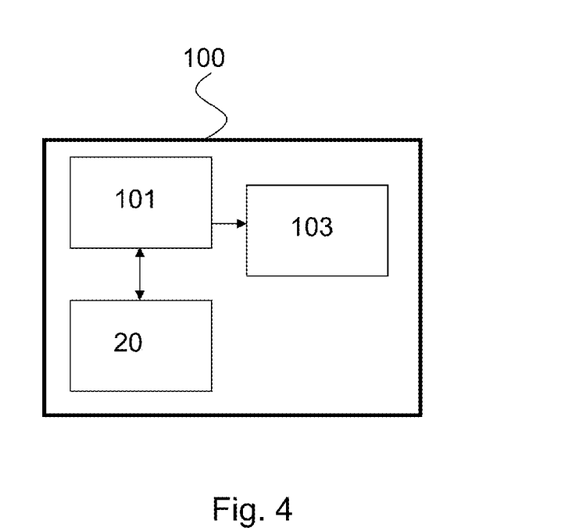
FIG. 4 shows a schematic representation of the device of the invention.

FIG. 4 shows a preferred embodiment of the device 100. It comprises pre-processing means 101 configured for providing one or more reference ion beamlets. Preferably, said pre-processing means execute an algorithm programmed for providing said one or more reference ion beamlets. Other or same pre-processing means 101 allows determining in a phantom linearly-superposable quantities induced by said one or more reference ion beamlets entering said phantom 60. In the preferred embodiment of FIG. 4, it is assumed that same pre-processing means 101 allows providing the one or more reference ion beamlets and determining said linearly-superposable quantities. As shown in the preferred embodiment of FIG. 4, said linearly-superposable quantities are preferably saved in a library 20. Other or same pre-processing means 101 allows approximating said ion beam 10 as a weighted superposition of ion beamlets 15, said weighted superposition comprising weight coefficients that are preferably determined from a phase space of said ion beam 10. At least one (preferably all) of said ion beamlets 15 is (are) obtained by applying a roto-translation operation to a reference ion beamlet. Other or same pre-processing means 101 allows determining one or more roto-translated distributions of one or more linearly-superposable quantities induced by said one or more roto-translated ion beamlets, by roto-translating distributions of linearly-superposable quantities with the roto-translation operations used for obtaining the roto-translated ion beamlets. Last, processing means 103 allow determining physical and/or radiobiological quantities representing effects induced by a ion beam 10 by performing at least one weighted superposition of distributions of linearly-superposable quantities, said at least one weighted superposition comprising weight coefficients used for approximating ion beam 10 as a weighted superposition of ion beamlets 15, and at least one distributions of linearly-superposable quantities being a roto-translated distribution determined previously. Preferably, said processing means 103 execute an algorithm programmed for performing said at least one weighted superposition. According to a preferred embodiment, pre-processing means 101 and processing means 103 are a same computing unit. Preferably, said pre-processing means 101 is a central processing unit (CPU) or another type of processor known by the one skilled in the art. Preferably, said processing means 103 is also a central processing unit (CPU) or another type of processor known by the one skilled in the art. Other examples for said pre-processing means 101 and/or said processing means 103 are: a controller, a ship, a microchip, an integrated circuit (IC), a multi-core processor, a system on chip (SoC), a control unit (for instance of a CPU), an array (or vector) processor.

The method and the device of the invention are preferably used for estimating the effect (or equivalently for computing physical and/or radiobiological quantities) induced by a therapeutic ion beam 10. However, they could be used for modelling other problematics related to the interaction of energetic particles with matter. Ion beam 10 is preferably delivered through a beam scanning technique. However, method and device of the invention also apply for other types of ion beams 10.

The present invention has been described in terms of specific embodiments, which are illustrative of the invention and not to be construed as limiting. More generally, it will be appreciated by persons skilled in the art that the present invention is not limited by what has been particularly shown and/or described hereinabove. Reference numerals in the claims do not limit their protective scope. Use of the verbs "to comprise", "to include", "to be composed of", or any other variant, as well as their respective conjugations, does not exclude the presence of elements other than those stated. Use of the article "a", "an" or "the" preceding an element does not exclude the presence of a plurality of such elements.

The method of the invention may also be summarized as follows. Method comprising the steps of: providing a reference ion beamlet; determining in a phantom 60 a distribution of a linearly-superposable quantity representing a linearly-superposable effect induced by said reference ion beamlet; approximating an ion beam 10 as a weighted superposition of ion beamlets 15, said weighted superposition comprising weight coefficients, at least one ion beamlet 15 being obtained by applying a roto-translation operation to said reference ion beamlet; determining a roto-translated distribution of a linearly-superposable quantity by roto-translating said distribution of a linearly-superposable quantity with said roto-translation operation; determining said physical and/or radiobiological quantities by performing a weighted superposition comprising said weight coefficients, and said roto-translated distribution of a linearly-superposable quantity.

The invention claimed is:

1. A method for computing a physical or a radiobiological quantity representing an effect induced in a volume by an ion beam entering said volume, said method comprising the steps of:
   a) providing a reference ion beamlet representing an elementary ion beam and providing a phantom;
   b) determining in said phantom, by executing instructions embodied on a machine readable medium, a distribution of a linearly-superposable quantity representing a linearly-superposable effect induced by said reference ion beamlet entering said phantom;
   c) approximating, by executing instructions embodied on a machine readable medium, said ion beam as a weighted superposition of ion beamlets,
      i) one of said ion beamlets being a roto-translated ion beamlet that is obtained by applying a roto-translation operation to said reference ion beamlet, a roto-translation operation comprising an operation of at least one of rotation or translation,
      ii) said weighted superposition comprising weight coefficients;
   d) applying, by executing instructions embodied on a machine readable medium, the roto-translation operation of step c)i) to the distribution of a linearly-superposable quantity of step b) for obtaining a roto-translated distribution of the linearly-superposable quantity representing an effect induced by the roto-translated ion beamlet of step c)i); and
   e) performing, by executing instructions embodied on a machine readable medium, a weighted superposition comprising the roto-translated distribution of previous step d), and weight coefficients of step c)ii), for obtaining said physical or radiobiological quantity.

2. The method according to claim 1 wherein:
said ion beam is characterized by a phase space; and
said weight coefficients of step c)ii) are determined from a discretization of said phase space.

3. The method according to claim 2 wherein:
said phase space of said ion beam comprises a longitudinal phase space, $f_L$, comprising an energy distribution, $g(E)$; and
said weight coefficients of step c)ii) comprise energy weight coefficients, $g_{E,l}$, determined from a discretization of said energy distribution, $g(E)$.

4. The method according to claim 2 wherein:
said phase space of said ion beam comprises a longitudinal phase space, $f_L$, comprising a main Water Equivalent Thickness (WET) distribution, $w(z)$, for taking into account presence of a material traversed by said ion beam before reaching said volume; and
said weight coefficients of step c)ii) comprise WET weight coefficients, $w_l$, determined from a discretization of said main WET distribution, $w(z)$.

5. The method according to claim 2 wherein:
said phase space of said ion beam comprises a transversal phase space; and
said weight coefficients of step c)ii) comprise transversal weight coefficients determined from a discretization of said transversal phase space and beam optics calculations.

6. The method according to claim 1 comprising further a step of scaling for taking into account differences in path lengths when said ion beam enters said phantom or when said ion beam enters said volume.

7. The method according claim 1 further comprising the steps of:
determining a water equivalent path mapping between path lengths in said volume and path lengths in said phantom; and
applying said water equivalent path mapping to the distribution of a linearly-superposable quantity of step b).

8. The method according to claim 1 further comprising a step of determining a water equivalent path mapping between path lengths of said ion beam in said volume and path lengths of same ion beam in said phantom, and wherein said water equivalent path mapping is applied to the result of step e).

9. The method according claim 1 wherein said distribution of a linearly-superposable quantity is determined in step b) with Monte Carlo simulations.

10. The method according to claim 1 wherein said distribution of a linearly-superposable quantity is a distribution of mean dose per unit fluence.

11. The method according to claim 1 wherein said distribution of a linearly-superposable quantity is a distribution of mean track fluence per primary or a distribution of mean energy transfer density per primary or a distribution of mean dose-weighted energy transfer density per primary.

12. The method according to claim 1 wherein said distribution of a linearly-superposable quantity is a distribution of average number of lethal events per primary depending on a, where a is a parameter entering a Linear-Quadratic law for taking into account radiobiological effectiveness of an ion beam.

13. The method according to claim 1 wherein said distribution of a linearly-superposable quantity is a distribution of square root of average number of lethal event per primary depending on $\beta$, where $\beta$ is a parameter entering a Linear-Quadratic law for taking into account radiobiological effectiveness of an ion beam.

14. The method according to claim 1 wherein ion beamlets of step c) have different energy distributions.

15. A device for computing a physical or a radiobiological quantity representing an effect induced in a volume by an ion beam entering said volume, said device comprising:
pre-processing means configured for providing a reference ion beamlet representing an elementary ion beam;
pre-processing means configured for determining in a phantom a distribution of a linearly-superposable quantity representing a linearly-superposable effect induced by said reference ion beamlet entering said phantom;
pre-processing means configured for approximating said ion beam as a weighted superposition of ion beamlets,
   i) one of said beamlets being a roto-translated ion beamlet that is obtained by applying a roto-translation operation to said reference ion beamlet, a roto-translation operation comprising an operation of at least one of rotation or translation,
ii) said weighted superposition comprising weight coefficients;

pre-processing means configured for roto-translating said distribution of a linearly-superposable quantity with said roto-translation operation, for obtaining a roto-translated distribution of same linearly-superposable quantity; and processing means configured for performing a weighted superposition comprising said roto-translated distribution and weight coefficients used in the weighted superposition for approximating said ion beam, for obtaining said physical or radiobiological quantity.

* * * * *